United States Patent
Teague et al.

(10) Patent No.: US 9,789,293 B2
(45) Date of Patent: Oct. 17, 2017

(54) STENTS WITH BLADDER RETENTION MEMBERS

(75) Inventors: James Teague, Spencer, IN (US); Travis Deal, Freedom, IN (US); Nancy Deal, legal representative, Freedom, IN (US); John Lingeman, Bloomington, IN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 471 days.

(21) Appl. No.: 13/156,827

(22) Filed: Jun. 9, 2011

(65) Prior Publication Data

US 2011/0320008 A1  Dec. 29, 2011

Related U.S. Application Data

(60) Provisional application No. 61/358,223, filed on Jun. 24, 2010.

(51) Int. Cl.
*A61F 2/04* (2013.01)
*A61M 27/00* (2006.01)

(52) U.S. Cl.
CPC ............. *A61M 27/008* (2013.01); *A61F 2/04* (2013.01); *A61F 2002/047* (2013.01); *A61F 2002/048* (2013.01); *A61F 2250/0018* (2013.01); *A61F 2250/0019* (2013.01); *A61F 2250/0029* (2013.01)

(58) Field of Classification Search
CPC ................. A61F 2/04; A61F 2002/048; A61F 2002/047; A61M 5/00; A61M 27/008
USPC .............................. 604/8–9; 623/23.64–23.71
See application file for complete search history.

(56) References Cited

U.S. PATENT DOCUMENTS

| | | | |
|---|---|---|---|
| 5,613,950 A | 3/1997 | Yoon | |
| 6,719,804 B2 * | 4/2004 | St. Pierre | 623/23.7 |
| 6,764,519 B2 | 7/2004 | Whitmore, III | |
| 7,037,345 B2 | 5/2006 | Bottcher et al. | |
| 7,169,139 B2 * | 1/2007 | Teague et al. | 604/524 |
| 7,252,674 B2 | 8/2007 | Wyzgala et al. | |
| 2004/0181186 A1 * | 9/2004 | Gellman et al. | 604/8 |
| 2006/0259151 A1 * | 11/2006 | Ward | 623/23.7 |
| 2006/0264912 A1 * | 11/2006 | McIntyre | A61K 9/0034 604/891.1 |
| 2008/0071384 A1 * | 3/2008 | Deal | A61L 31/041 623/23.66 |
| 2008/0077250 A1 * | 3/2008 | Amos | 623/23.66 |
| 2008/0183299 A1 * | 7/2008 | Monga et al. | 623/23.66 |

FOREIGN PATENT DOCUMENTS

WO    2011163127 A1    12/2011

OTHER PUBLICATIONS

Search Report and Written Opinion for International Application No. PCT/US2011/041071, mailed Oct. 14, 2011, 11 pages.

* cited by examiner

*Primary Examiner* — Andrew Iwamaye

(57) ABSTRACT

A medical device including an elongate member having a distal end portion, a proximal end portion, and a medial portion disposed between the distal end portion an the proximal end portion. The proximal end portion is configured to be disposed within a bladder of a patient. A portion of the proximal end portion is configured to contact an inner wall of the bladder to help retain the bladder in an expanded configuration.

13 Claims, 15 Drawing Sheets

STENTS WITH BLADDER RETENTION MEMBERS

CROSS-REFERENCE TO RELATED APPLICATION

This application is a Nonprovisional of, and claims priority to, U.S. Patent Application No. 61/358,223, filed Jun. 24, 2010, entitled "STENTS WITH BLADDER RETENTION MEMBERS", which is incorporated by reference herein in its entirety.

TECHNICAL FIELD

This disclosure relates generally to medical devices for draining fluids, and more specifically to stents including ureteral stents that are configured to extend from a kidney of a patient to a bladder of a patient.

BACKGROUND

Medical devices are often used to drain fluids within a patient's body. For example, ureteral stents can be used to assist the drainage of fluids through the urinary system of a patient. Some known ureteral stents include a tubular member and are configured to assist the drainage of fluid from one part of the urinary system to another part of the urinary system. Some known ureteral stents are configured to extend from a patient's kidney to a patient's bladder. Such known ureteral stents assist to drain fluid from the patient's kidney to the patient's bladder.

Regions of the urinary system are particularly sensitive and are prone to irritation by foreign objects. Thus, to avoid patient irritation and pain, it may be advantageous to provide urinary stents that either avoid contact with the sensitive regions of the patient or otherwise provide a stent that does not irritate such sensitive regions. For example, one particularly sensitive region of the urinary system is the trigone region, which is located within the bladder of the patient. Thus, it may be advantageous to provide a urinary stent that either avoids contact with the trigone region or does not otherwise irritate the trigone region.

Additionally, some known urinary stents may be forced or pressured into the trigone region when the bladder is empty. For example, an empty bladder may collapse upon itself and force or pressure a urinary stent disposed within the patient into the trigone region of the patient causing irritation and/or pain and discomfort to the patient. Thus, it may be advantageous to provide a ureteral stent that distends the bladder or otherwise prevents the bladder from forcing or pressuring the ureteral stent into the trigone region of the patient.

SUMMARY

A medical device including an elongate member having a distal end portion, a proximal end portion, and a medial portion disposed between the distal end portion and the proximal end portion. The proximal end portion is configured to be disposed within a bladder of a patient. A portion of the proximal end portion is configured to contact the bladder to help retain the bladder in an expanded configuration.

In some embodiments, the proximal end portion includes a first arm and a second arm. The first arm is configured to contact an inner wall of the bladder of the patient at a first location. The second arm is configured to contact the inner wall of the bladder of the patient at a second location. The second location is different than the first location.

A medical device including an elongate member having a distal end portion, a proximal end portion, and a medial portion disposed between the distal end portion and the proximal end portion. The distal end portion includes a first material. The medial portion includes a second material. The proximal end portion includes a third material. The second material is softer than the first material, and the second material is softer than the third material.

DETAILED DESCRIPTION

Figure 1:
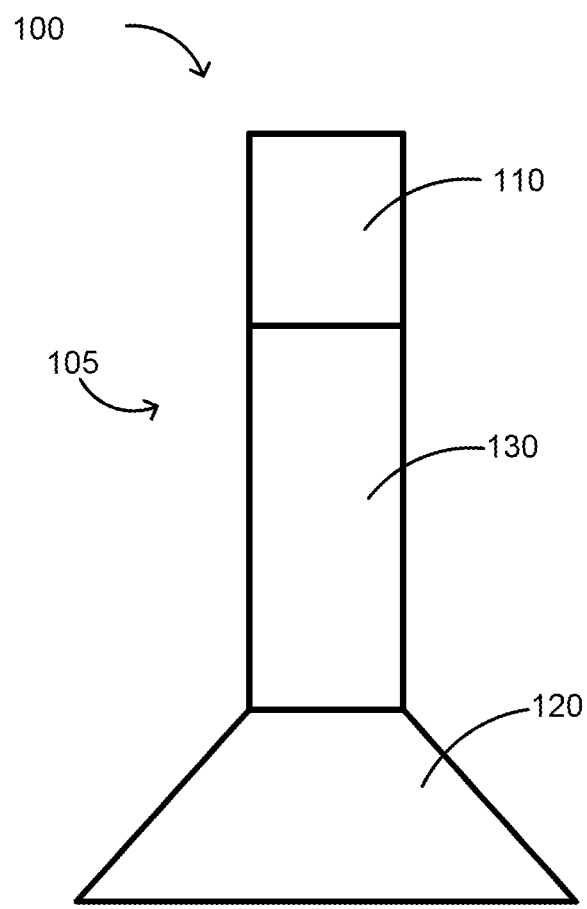
FIG. 1 is a schematic illustration of a medical device according to an embodiment of the invention.

FIG. 1 is a schematic view of an embodiment of a medical device 100. The medical device 100 includes an elongate member 105. The elongate member 105 has a distal end portion 110, a proximal end portion 120, and a medial portion 130. The medial portion 130 is disposed between the distal end portion 110 and the proximal end portion 120.

In one embodiment, the medical device 100 is a stent that is configured to be placed within a body of a patient and to help facilitate the drainage of fluid from one portion of the body to another portion of the body.

In one embodiment, the medical device 100 is a ureteral stent. In such an embodiment, the distal end portion 110 is configured to be disposed within a kidney of a patient and the proximal end portion 120 is configured to be disposed within a bladder of the patient. The medial portion 130 is configured to extend within a ureter of the patient. In such an embodiment, the medical device 100 is configured to help facilitate drainage of fluids such as urine within the urinary tract of the patient. Specifically, in such an embodiment, the medical device 100 is configured to facilitate drainage from the kidney of the patient to the bladder of the patient.

In some embodiments, the elongate member 105 of the medical device 100 defines a lumen extending from the distal end portion 110 to the proximal end portion 120. The lumen is configured to help facilitate the drainage of fluid within the body of the patient. Additionally, in some embodiments, side ports or openings are located along the length of the elongate member 105. The side ports or openings communicate with the lumen and further facilitate the drainage of fluid within the body.

In some embodiments, the proximal end portion 120 is configured to distend, expand, or otherwise retain a portion of the body of the patient in an expanded configuration. For example, in one embodiment, the proximal end portion 120 is configured to contact an inner surface of the patient's bladder to expand the bladder or to help retain the bladder in an expanded configuration. In other embodiments, the proximal end portion 120 is configured to retain a different portion of the patient's body in an expanded configuration.

In some embodiments, the proximal end portion 120 causes the bladder to feel full and thus prevent the bladder from collapsing. For example, in some embodiments of the medical device 100, the amount of material disposed in the bladder causes a "full" sensation within the bladder and thus prevents the bladder from collapsing or folding.

In some embodiments, the medical device 100 is configured to avoid contact with sensitive regions within the body of the patient. For example, in one embodiment, the medical device 100 (including the proximal end portion 120) is configured to avoid contact with the trigone region of the patient when the proximal end portion 120 of the medical device 100 is disposed within the bladder of a patient. For example, the proximal end portion 120 may be shaped such that it does not contact the trigone region of the patient. Additionally, in some embodiments, the retention of the bladder in an expanded configuration prevents movement of the medical device 100 (including the proximal end portion 120) into the trigone region of the patient. Specifically, in some embodiments, the retention of the bladder in an expanded configuration prevents the bladder from contracting (for example, when it is empty) or folding over on itself and forcing the medical device 100 into the trigone region.

In some embodiments, the distal end portion 110 includes a retention member configured to help retain the medical device 100 in place within the body of the patient. For example, in some embodiments, the distal end portion 110 includes a retention member that is configured to be place within a kidney of the patient to help retain the medical device 100 in place within the urinary tract of the patient.

The medical device 100 may be place within the body of a patient using any known placement method. For example, the medical device 100 may be placed within the urinary tract of a patient using a guidewire to guide the medical device 100 into place within the body of the patient. Additionally, an insertion tube may be used to place the medical device within the body of the patient.

In some embodiments, the medical device 100 is constructed of a biocompatible material. For example, in some embodiments, the medical device 100 is constructed of a biocompatible plastic, such as, but not limited to, polyester, nylon based biocompatible polymers, polytetrafluoroethylene polymers, silicone polymers, polyurethane polymers, polyethylene polymers, and thermoplastic polymers. In one embodiment, the medical device is constructed of ethylene vinyl acetate.

The medical device 100 may be formed using any known construction method. For example, in some embodiments, the medical device 100, including the distal end portion 110, the medial portion 130, and the proximal end portion 120 are monolithic or unitarily formed. In such embodiments, the medical device 100 may be formed using an extrusion technique or an injection molding technique. In other embodiments, the medical device 100 is not monolithic or unitarily formed. In such embodiments, the different portions of the medical device 100 maybe coupled together using any known method.

The medical device 100 may be sized to appropriately fit within the body of the patient. For example, in some embodiments, the medical device 100 is sized such that the distal end portion 110 may be disposed in a kidney of a patient, the proximal end portion 120 may be disposed in a bladder of a patient, and the medial portion 130 may be disposed within a ureter of a patient. The medical device 100 can be of any diameter. For example, in some embodiments, the medial portion 130 has an outer diameter of between 4 French and 12 French. In other embodiments, the outer diameter of the medial portion is smaller than 4 French or greater than 12 French.

In some embodiments, a portion of the medical device 100 may extend from the body of the patient once it is placed within the body of the patient. In such embodiments, the medical device 100 may be configured to help convey fluid from one portion of the body to a location outside of the body of the patient.

Figure 2A:
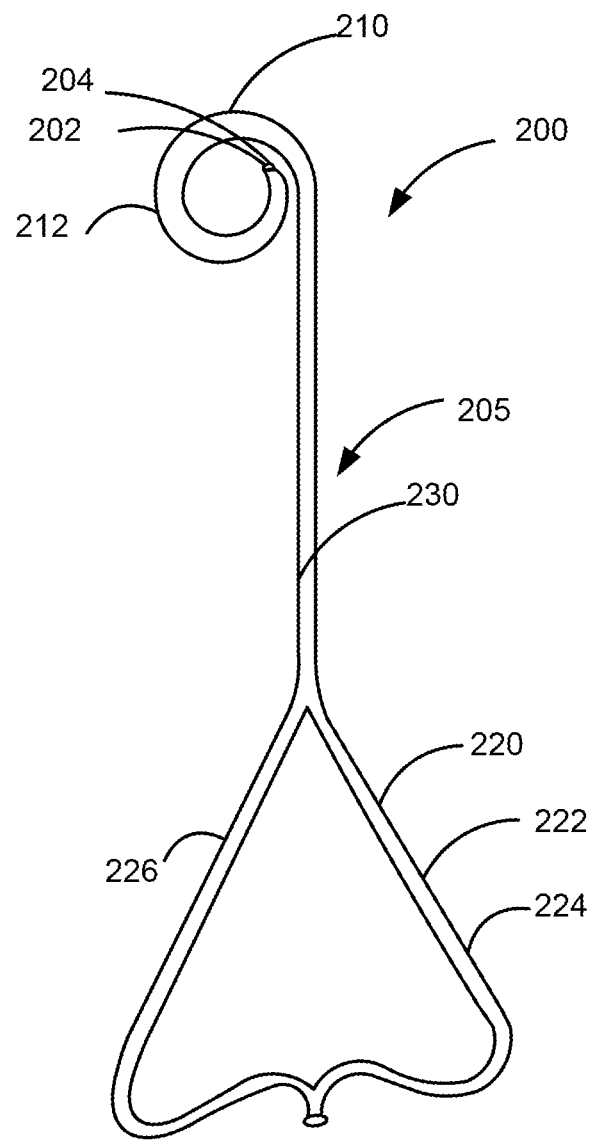
FIG. 2A is a perspective view of a stent according to an embodiment of the invention.
Figure 2B:
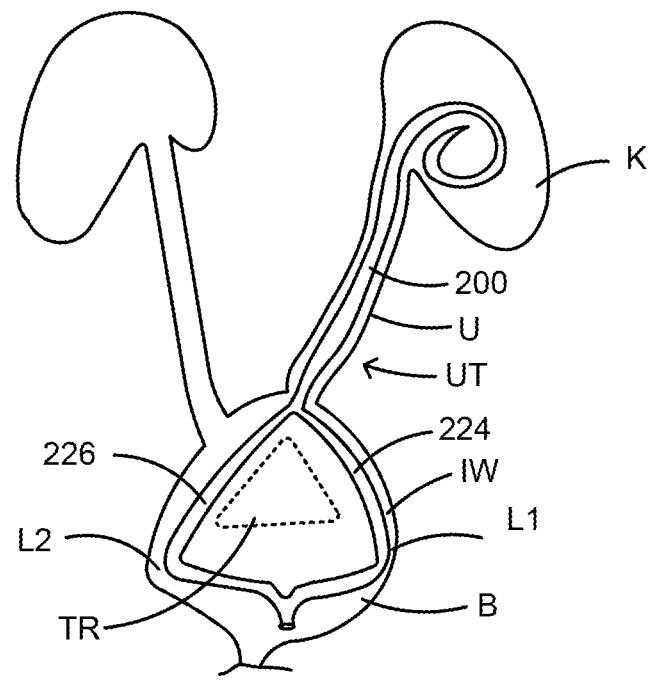
FIG. 2B is a schematic view of the stent of FIG. 2 disposed within the body of a patient.

FIG. 2A is a perspective view of a medical device 200 and FIG. 2B is a schematic view of the medical device 200 disposed within a body of a patient. The medical device 200 includes an elongate member 205. In the illustrated embodiment, the elongate member 205 is a tubular member with a circular cross-section. In other embodiments, the elongate member is of a different shape and has a different shaped cross-section (such as triangular, rectangular, or square).

The elongate member 205 has a distal end portion 210, a proximal end portion 220, and a medial portion 230 disposed between the distal end portion 210 and the proximal end portion 220. The medical device 200 is configured to be placed in the urinary tract UT of a patient and is configured to help convey fluid (such as urine) through the urinary tract.

The distal end portion 210 is configured to be placed in a kidney K of a patient. The distal end portion 210 includes a retention member 212. The retention member 212 is configured to be placed in a kidney K of a patient and to help retain the medical device 200 in place within the patient. In the illustrated embodiment, the retention member is a coil. In other embodiments, the retention member has a different shape.

The proximal end portion 220 is configured to be placed in a bladder B of the patient. The proximal end portion 220 is configured to distend or otherwise help retain the bladder B in an expanded configuration. Specifically, the proximal end portion 220 is configured to contact an inner wall IW of the bladder B to help retain the bladder B in an expanded configuration. Accordingly, in some embodiments, the proximal end portion 220 is configured to prevent the bladder B from collapsing upon itself when the bladder B is empty.

In the illustrated embodiment, the proximal end portion 220 includes a first arm 224 and a second arm 226 that form a malecot 222. As best illustrated in FIG. 2B, the first arm 224 is configured to contact the inner wall IW of the bladder B at a first location L1. The second arm 226 is configured to contact the inner wall IW of the bladder B at a second location L2. The second location L2 of the inner wall IW is different than the first location L1 of the inner wall IW.

The malecot 222 may be formed by any known method. For example, in one embodiment, the malecot 222 is formed by slicing or cutting slots in the elongate member 205. In other embodiments, the malecot 222 is formed by forming or molding an elongate member with longitudinal slots.

Although in the illustrated embodiment, the first arm 224 of the proximal end portion 220 is coupled to the second arm 226 of the proximal end portion 220 at two locations X and Y, in other embodiments, the first arm is not coupled to the second arm at two locations. For example, in some embodiments, the first arm and the second arm are only coupled together at a first location. In such an embodiment, an end portion of the first arm is disposed apart from an end portion of the second arm when the medical device is disposed within the body of the patient.

In one embodiment, the arms 224 and 226 are sufficiently resilient to distend or otherwise maintain the bladder B in an expanded configuration. In some embodiments, the arms 224 and 226 include nitinol, such as a nitinol wire. In other embodiments, the arms 224 and 226 include a reinforcement material to provide the necessary resiliency.

The medial portion 230 is configured to be disposed within the ureter U of the patient. The elongate member 205 defines a lumen 202 that from the distal end portion 210 and through the medial portion 230. The lumen 202 is configured to convey fluid from the kidney K to the bladder B of the patient. In the illustrated embodiment, the lumen 202 extends from opening 204 defined by the distal portion 210 of the medical device 200 to the proximal end portion 220. In some embodiments, the elongate member 205 includes side ports or openings that communicate with the lumen to further assist the fluid flow within the body of the patient.

As best illustrated in FIG. 2B, the medical device 200 is configured to avoid or otherwise minimize contact with the trigone region TR of the patient. Specifically, as described above, the arms 224 and 226 are configured to contact the inner wall IW of the bladder B of the patient and thus, extend away from the trigone region TR of the patient. Additionally, as the described above, in some embodiments, the arms 224 and 226 are sufficiently resilient to retain the bladder B in an extended configuration, and thus, are configured to help prevent the bladder B from collapsing and forcing a portion of the medical device 200 into contacting the trigone region TR of the patient.

The medical device 200 can be inserted or placed within a body of a patient using any known method. For example, the medical device can be placed by placing a guidewire into the body of the patient and moving the medical device 200 along the guidewire (by extending the guidewire through the lumen 202 defined by the elongate member 205). As will be described in more detail below, to facilitate placement of the medical device 200 into the body, the arms 224 and 226 of the malecot 222 can be placed in a collapsed configuration. For example, in some embodiments, the arms 224 and 226 of the malecot 222 may be placed in a collapsed configuration using an insertion tube.

Although the medical device 200 is illustrated as including a proximal end portion 220 that has two arms 224 and 226, the proximal end portion may include any number of arms.

Figure 3:
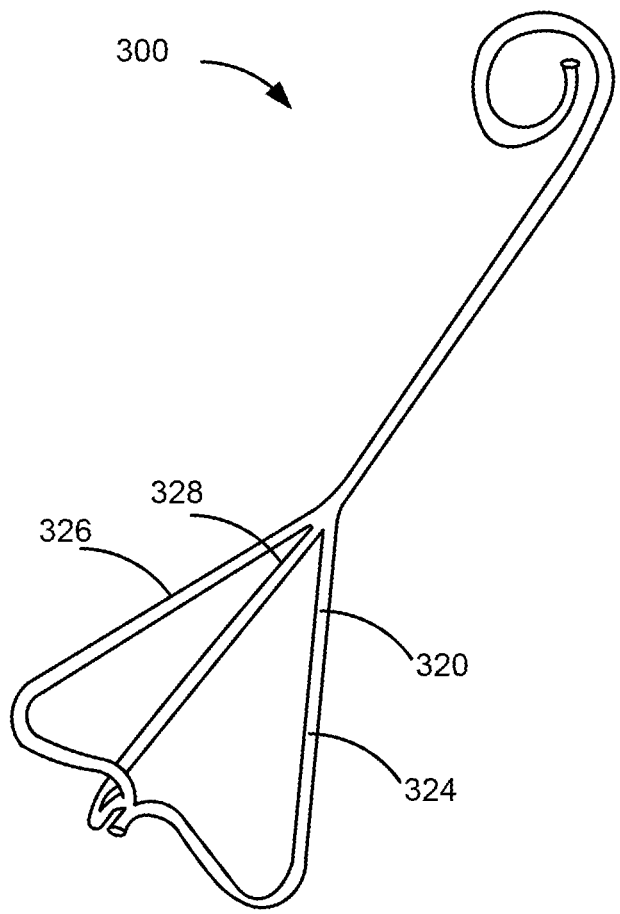
FIGS. 3-6 are perspective views of a stents according to embodiments of the invention.

As illustrated in FIG. 3, in one embodiment, a medical device 300 includes a proximal end portion 320 that has a first arm 324, a second arm 326, and a third arm 328. The proximal end portion 320 is configured to be disposed within a bladder of a patient such that the first arm 324 contacts the inner wall of the bladder at a first location, the second arm 326 contacts the inner wall of the bladder at a second location, and the third arm 328 contacts the inner wall of the bladder at a third location. The arms 324, 326, and 328 are collectively configured to distend the bladder or otherwise retain the bladder in an expanded configuration.

Figure 4:
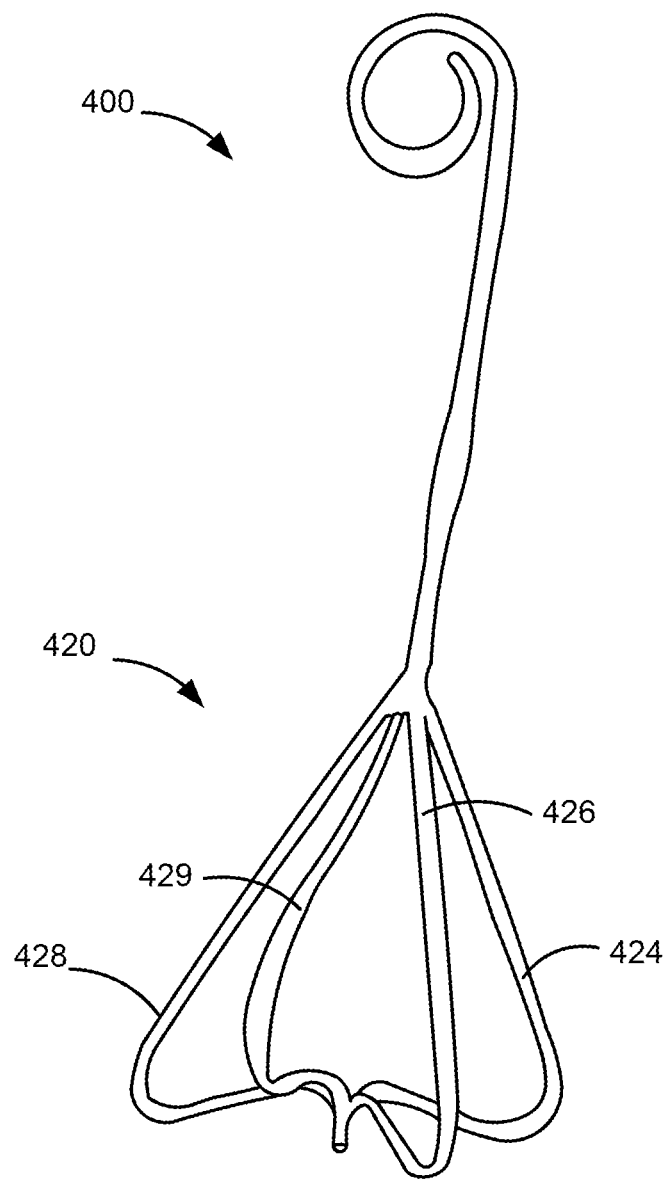

As illustrated in FIG. 4, in one embodiment, a medical device 400 includes a proximal end portion 420 that has a first arm 424, a second arm 426, a third arm 428, and a fourth arm 429. The proximal end portion 420 is configured to be disposed within a bladder of a patient such that the first arm 424 contacts the inner wall of the bladder at a first location, the second arm 426 contacts the inner wall of the bladder at a second location, the third arm 428 contacts the inner wall of the bladder at a third location, and the fourth arm 429 contacts the inner wall of the bladder at a fourth location. The arms 424, 426, 428, and 429 are collectively configured to distend the bladder or otherwise retain the bladder in an expanded configuration.

Figure 5:
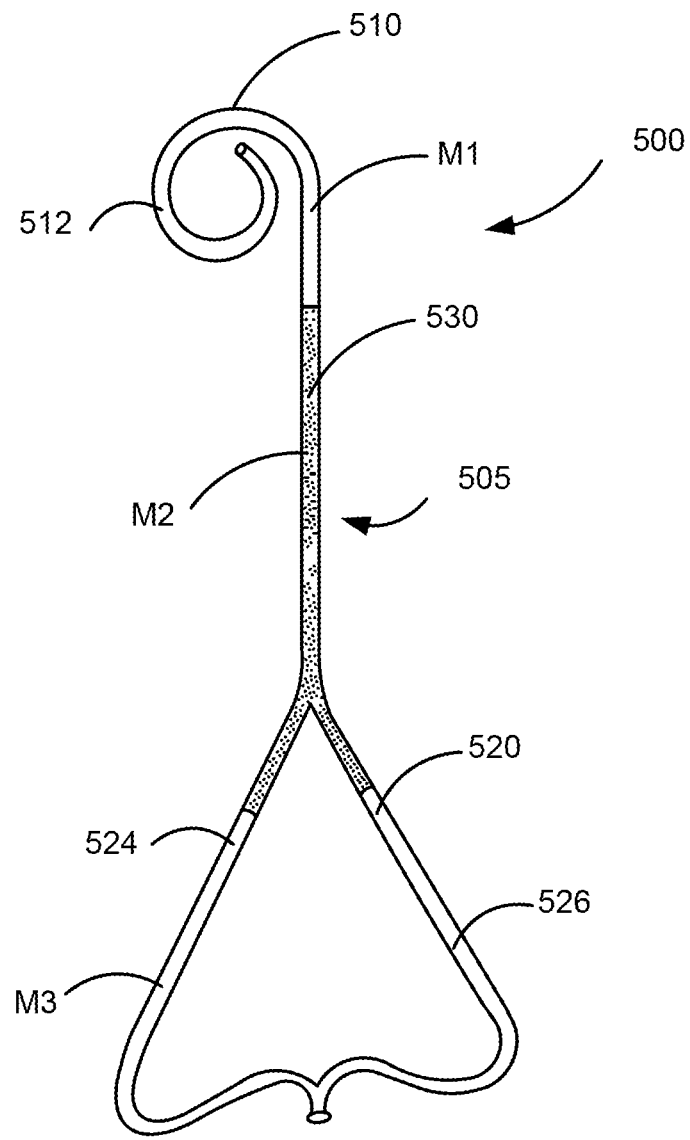

FIG. 5 is a perspective view of a medical device 500. The medical device 500 includes an elongate member 505 that has a distal end portion 510, a proximal end portion 520, and a medial portion 530. In one embodiment, the medical device 500 is a ureteral stent and is configured to help facilitate the flow of fluid from one portion of the body to another portion of the body.

The distal end portion 510 is configured to be placed in a kidney of the patient and includes a retention member 512. The retention member 512 is configured to help retain the medical device 500 in place within the body of the patient.

The proximal end portion 520 is configured to be placed in a bladder of the patient and is configured to distend or otherwise retain the bladder in an expanded configuration. The proximal end portion 520 includes arms 524 and 526 that are configured to contact the bladder to help retain the bladder in an expanded configuration.

The medical device 500 is composed of multiple materials. The distal end portion 510 includes a first material M1, the medial portion 530 includes a second material M2, and the proximal end portion 520 includes a third material M3. Although a portion of arms 524 and 526 are illustrated as being constructed of the second material SM, in other embodiments, the arms 524 and 526 are entirely constructed of the third material M3.

The first material M1 is configured to be stiff enough or hard enough to help retain the medical device 500 in place within the body. The second material M2 is configured to be softer than the first material M1. The third material M3 is configured to be harder than the second material M2 and is configured to be sufficiently resilient to help retain the bladder in an expanded configuration.

In one embodiment, the second material M2 has a lower durometer than the first material M1. The second material M2 also has a lower durometer than the third material M3. For example, in one embodiment, the first material M1 has a durometer of between 86 and 90 shore A, the second material M2 has a durometer of between 82 and 86 shore A, and the third material M3 has a durometer of between 86 and 95 shore A. In other embodiments, the materials are harder or softer than the above ranges.

In one embodiment, the first material M1 is a different material than the third material M3. In another embodiment, the first material M1 is the same as the third material M3. For example, in some embodiments, the materials M1, M2, and M3 are biocompatible plastics, such as, but not limited to, polyester, nylon based biocompatible polymers, polytetrafluoroethylene polymers, silicone polymers, polyurethane polymers, polyethylene polymers, and thermoplastic polymers.

In some embodiments, medical device 500 is constructed using a co-extrusion method. For example, the medical device may be constructed as described in U.S. Pat. No. 6,719,804, which is hereby incorporated by reference in its entirety.

Figure 6:
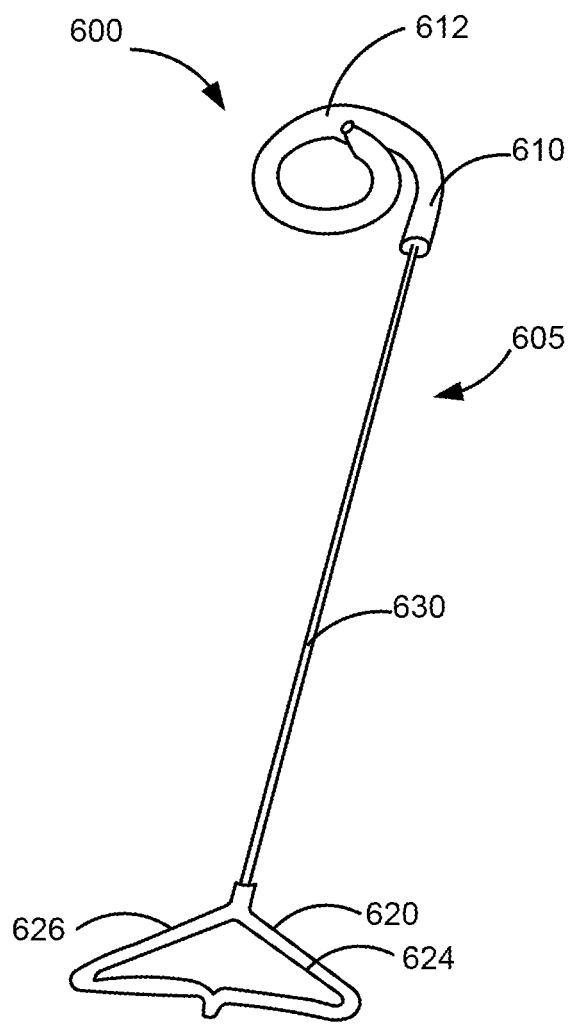

FIG. 6 is a perspective view of a medical device 600. The medical device 600 includes an elongate member 605 that has a distal end portion 610, a proximal end portion 620, and a medial portion 630. In one embodiment, the medical device 600 is a ureteral stent and is configured to help facilitate the flow of fluid from one portion of the body to another portion of the body.

The distal end portion 610 is configured to be placed in a kidney of the patient and includes a retention member 612.

The retention member 612 is configured to help retain the medical device 600 in place within the body of the patient.

The medial portion 630 extends from the distal end portion 610 to the proximal end portion 620. The medial portion 630 is configured to be placed in the ureter of the patient. In some embodiments, the medial portion 630 is string-like and is thinner (or has a smaller diameter) than the distal end portion 610. In some embodiments, the medial portion 630 is substantially solid and transports fluid within the body via a wicking mechanism. In some embodiments, the medial portion 630 includes a porous material. In some embodiments, the medial portion 630 includes a material that is softer than the material of the distal end portion 610.

The proximal end portion 620 is configured to be placed in a bladder of the patient and is configured to distend or otherwise retain the bladder in an expanded configuration. The proximal end portion 620 includes arms 624 and 626 that are configured to contact the bladder to help retain the bladder in an expanded configuration.

Figure 7:
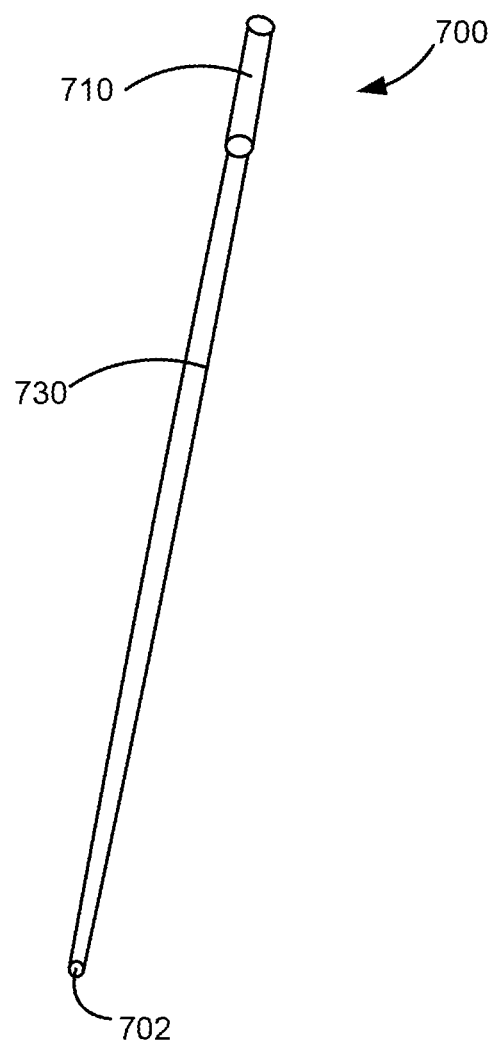
FIG. 7 is a perspective view of an insertion tube.

FIG. 7 is an insertion tube 700 that may be used to insert the medical device 600. The insertion tube 700 defines a lumen 702 that is configured to receive the medical device 600. The insertion tube 700 includes a distal portion 710 that is sized to receive the distal end portion 610 of the medical device 600. In some embodiments, the distal end portion 710 also provides an interface for being pushed or inserted into the body of the patient (as will be described in detail below). The insertion tube also includes a medial portion 730 that is configured to receive the medial portion 630 of the medical device 600. In the illustrated embodiment, the distal end portion 710 of the insertion tube 700 has a larger diameter than the medial portion of the insertion tube 730.

Figure 8:
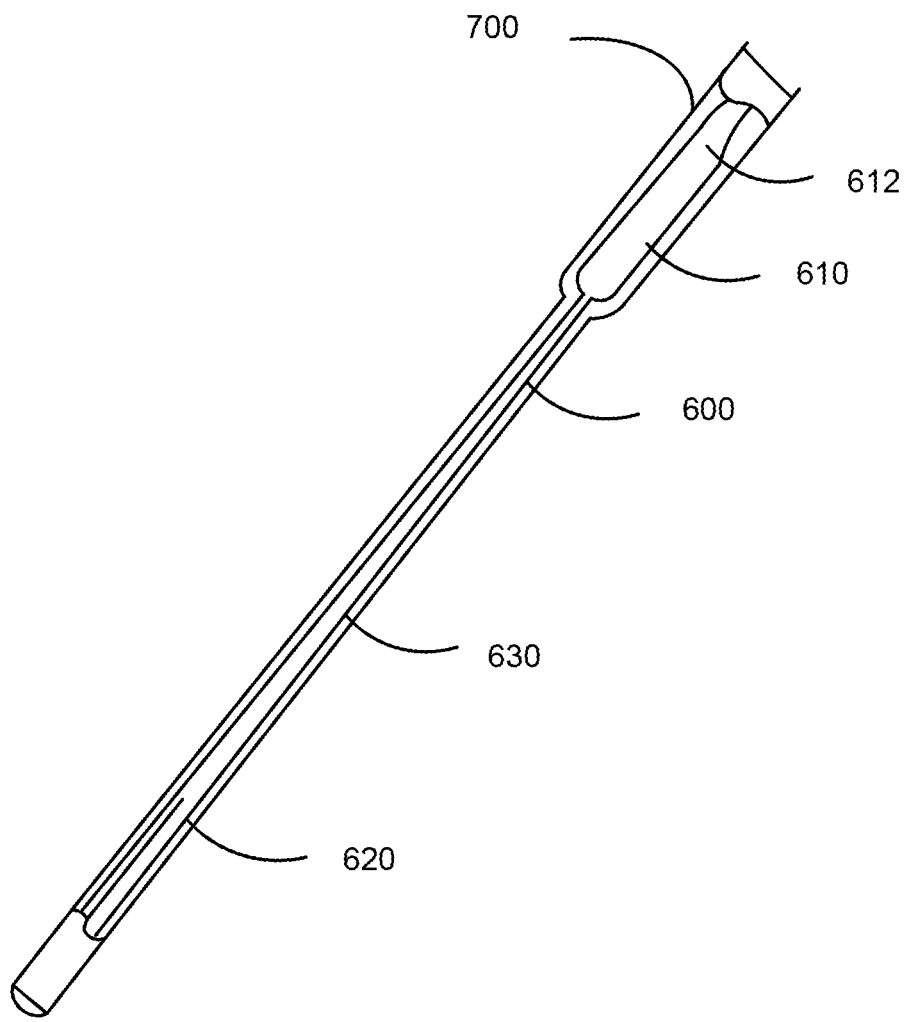
FIGS. 8 and 9 are perspective breakaway views of the stent of FIG. 6 disposed in the insertion tube of FIG. 7.
Figure 9:
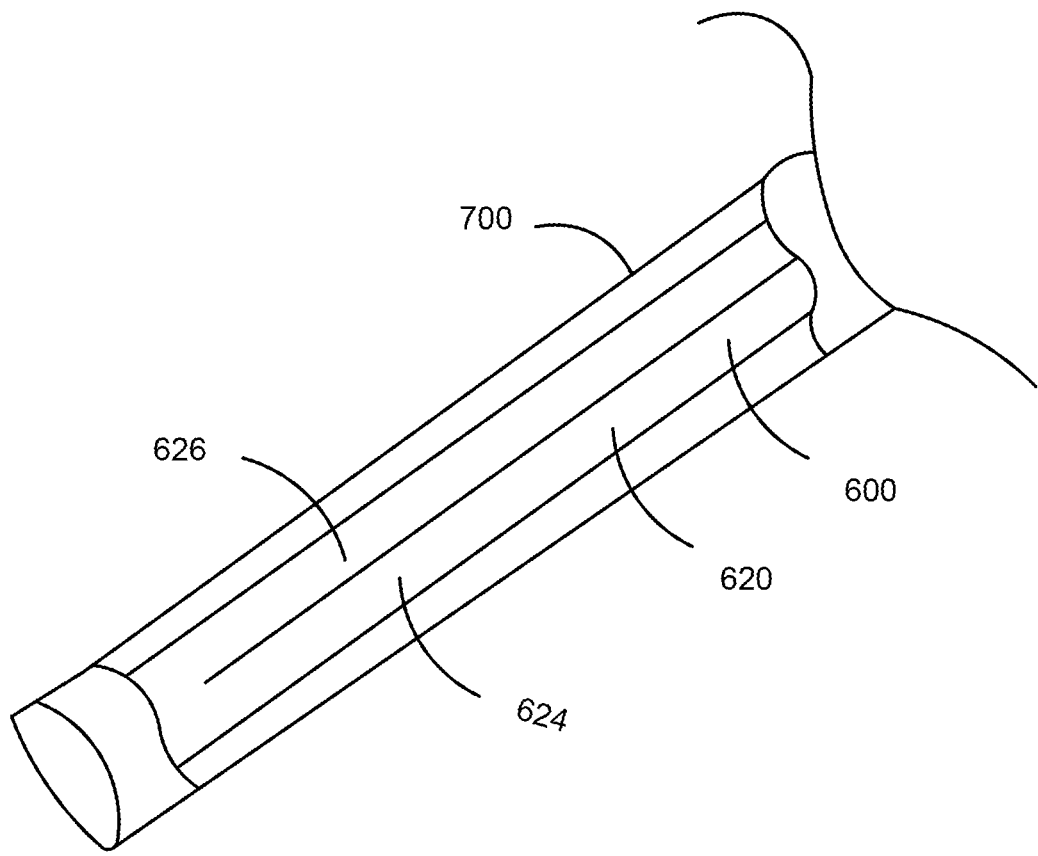

FIG. 8 is a perspective cut-away view of the medical device 600 disposed within the insertion tube 700. When the medical device 600 is disposed within the insertion tube 700, the medical device 600 assumes a substantially linear form. Specifically, the retention member 612 of the distal end portion 610 is placed in a substantially linear form. Similarly, as best illustrated in FIG. 9, the arms 624 and 626 of the proximal end portion 620 are extended to place the proximal end portion 620 in a substantially linear form.

The medial device 600 may be inserted into the insertion tube 700 as illustrated in FIG. 8 and then placed within the body using a scope. In another embodiment, the medical device 600 may be placed using the insertion tube 700 and a guidewire. In one embodiment, a pusher may be used to contact the distal end portion 710 of the insertion tube 700 to push the medical device 600 into place within the body of the patient. Once the medical device 600 is appropriately placed within the body, the insertion tube 700 and the guidewire may then be removed leaving the medical device 600 within the body.

Figure 10:
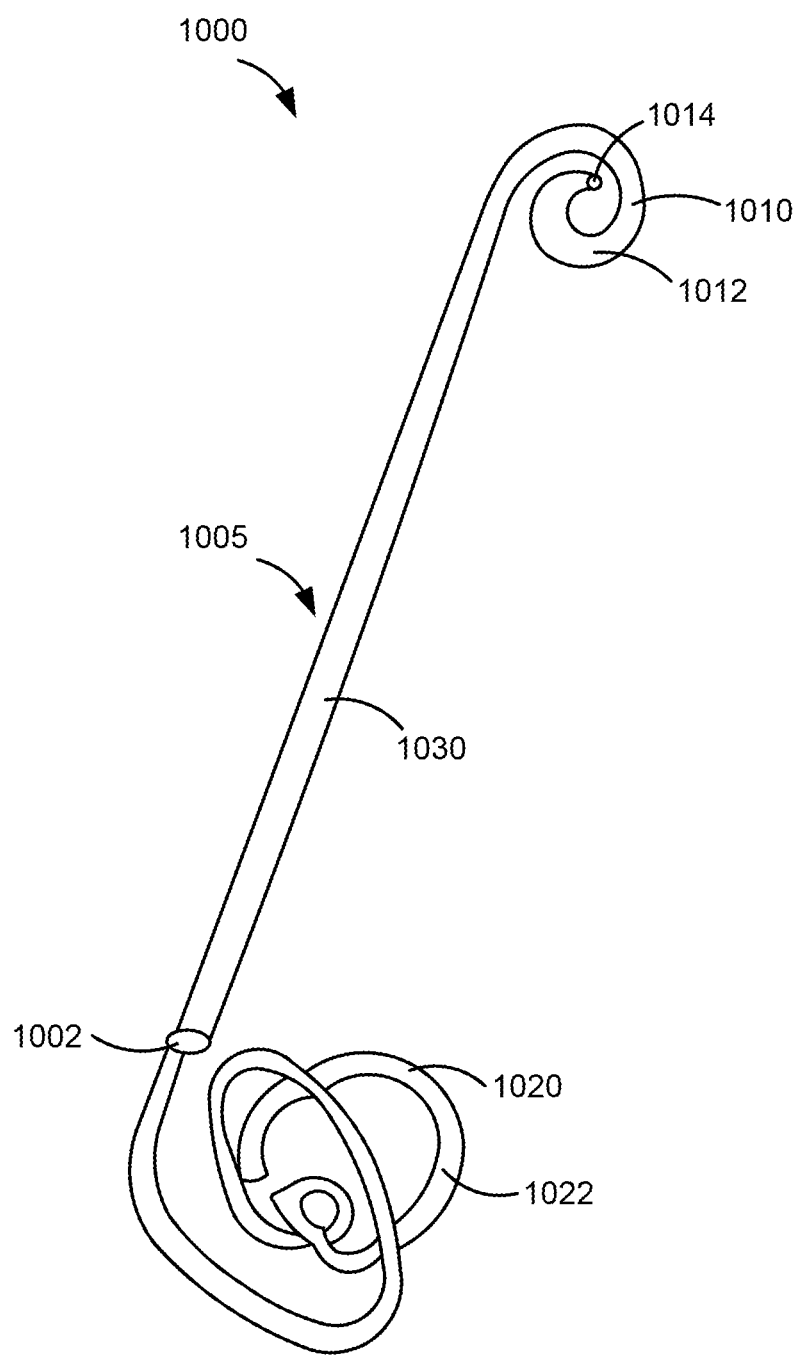
FIGS. 10-13 are perspective views of stents according to embodiments of the invention.

FIG. 10 is a perspective view of a medical device 1000. The medical device 1000 includes an elongate member 1005 that has a distal end portion 1010, a proximal end portion 1020, and a medial portion 1030. In one embodiment, the medical device 1000 is a ureteral stent and is configured to help facilitate the flow of fluid from one portion of the body to another portion of the body. In one embodiment, the elongate member 1005 defines a lumen that extends from an opening 1014 defined by the distal end portion 1010 to an opening 1002 defined by the proximal end portion 1020.

The distal end portion 1010 is configured to be placed in a kidney of the patient and includes a retention member 1012. The retention member 1012 is configured to help retain the medical device 1000 in place within the body of the patient.

The proximal end portion 1020 is configured to be placed in a bladder of the patient and is configured to distend or otherwise retain the bladder in an expanded configuration. The proximal end portion 1020 includes a wound portion 1022. As illustrated, the wound portion 1022 has a random pattern. In other embodiments, the wound portion has a symmetric or systematic pattern.

In one embodiment, the wound portion 1022 is configured to contact the bladder to distend or otherwise help retain the bladder in an expanded configuration. In some embodiments, the wound portion 1022 is configured to contact the bladder at various locations. Additionally, in some embodiments, the medical device 1000 (including the wound portion 1022) is configured to avoid contact with the trigone region of the patient.

The wound portion 1022 may be formed by any known method. In one embodiment, the wound portion 1022 is formed by thermosetting the material that forms the wound portion 1022. In another embodiment, the wound portion includes a flexible material and a reinforcement material, such as a nitinol wire, that is configured to provide resiliency and retain the shape of the wound portion 1022. In such an embodiment, the reinforcement material may be bound to a surface of the flexible material or may be embedded within the flexible material.

In one embodiment, the wound portion 1022 includes a malleable material, such as a wire, that may be shaped by a physician prior to or during placement of the medical device 1000 within the body of the patient. The physician may shape the wound portion 1022 to conform to the specific shape of the patient's body. For example, the physician may shape the wound portion 1022 to best conform to the shape of the bladder of the patient. Alternatively, the physician may shape the wound portion 1022 to best distend the bladder of the patient or to best avoid contacting the trigone region of the patient.

Figure 11:
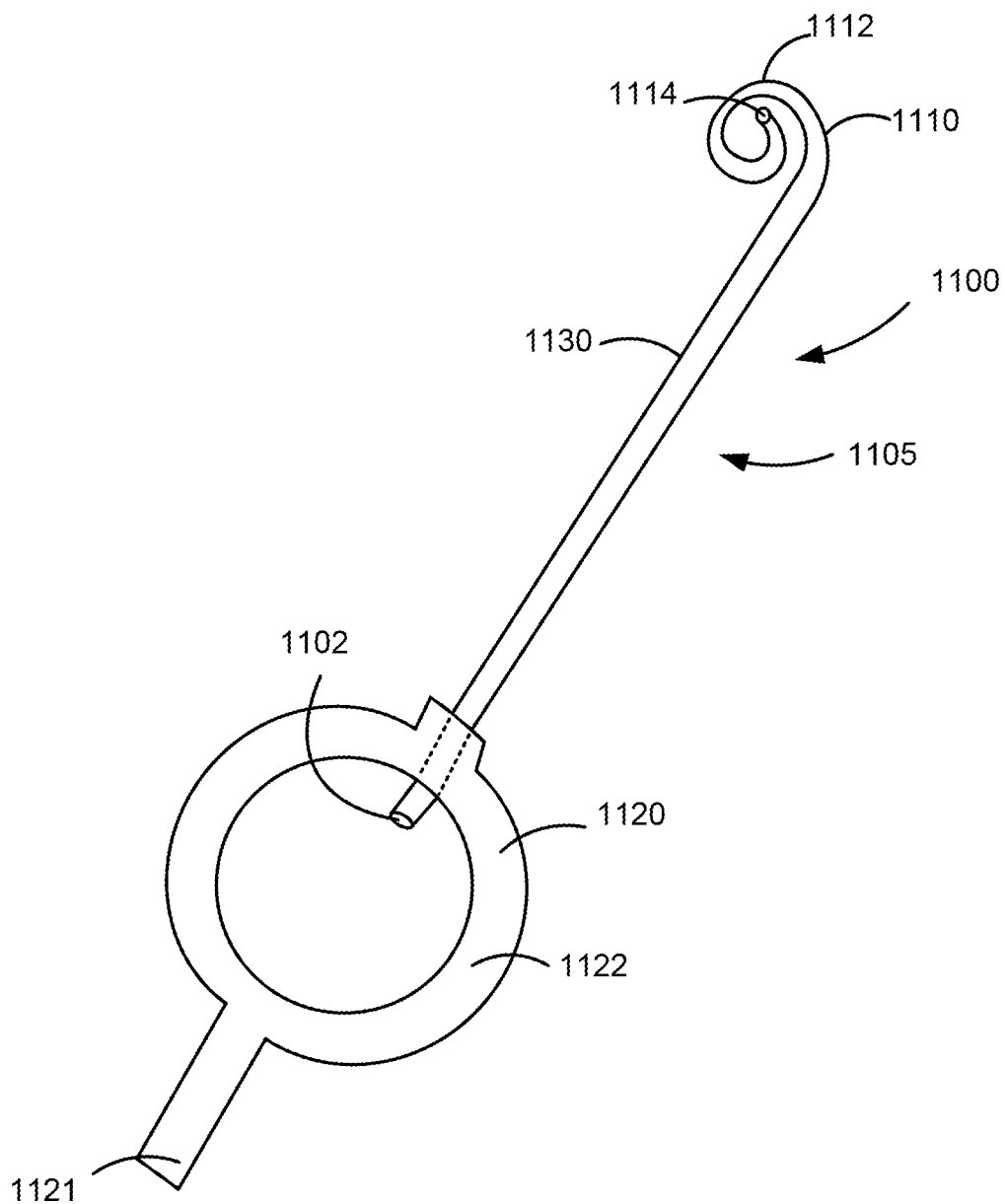

FIG. 11 is a perspective view of a medical device 1100. The medical device 1100 includes an elongate member 1105 that has a distal end portion 1110, a proximal end portion 1120, and a medial portion 1130. In one embodiment, the medical device 1100 is a ureteral stent and is configured to help facilitate the flow of fluid from one portion of the body to another portion of the body. In one embodiment, the elongate member 1105 defines a lumen that extends from an opening 1114 defined by the distal end portion 1110 to an opening 1102 defined by the proximal end portion 1120.

The distal end portion 1110 is configured to be placed in a kidney of the patient and includes a retention member 1112. The retention member 1112 is configured to help retain the medical device 1100 in place within the body of the patient.

The proximal end portion 1120 is configured to be placed in a bladder of the patient and is configured to distend or otherwise retain the bladder in an expanded configuration. The proximal end portion 1120 includes an inflatable portion 1122. For example, in one embodiment, the inflatable portion 1122 is an inflatable balloon. The inflatable portion 1122 is configured to contact an inner wall of the bladder of the patent to help retain the bladder in an expanded configuration. In some embodiments, the inflatable portion 1122 is configured to avoid contact with the trigone region of the patient when the proximal end portion is disposed within the bladder of the patient.

In some embodiments, the inflatable portion 1122 is configured to be inflated after the medical device 1100 has been placed within the body of the patient. In such embodiments, the inflatable portion 1122 may be inflated and oriented to appropriately contact the bladder of the patient and avoid contact with the trigone region of the patient.

The inflatable portion 1122 may be configured to be inflated by any known method. For example, in some embodiments, an inflation tool is inserted into the body after the medical device 1100 has been placed within the body to inflate the inflatable portion 1122. In one embodiment, the inflatable portion 1122 includes a valve to facilitate the inflation and deflation of the inflatable portion 1122. For example in one embodiment, the inflatable portion 1122 includes a ball check valve disposed at a proximal end 1121 of the medical device 1100.

The inflatable portion 1122 may be inflated with any biocompatible fluid. In some embodiments, the inflatable portion 1122 is inflated with a saline solution.

The inflatable portion 1122 may be constructed with any biocompatible material. For example, in some embodiments, the inflatable portion 1122 is constructed of an elastic material. In other embodiments, the inflatable portion 1122 is constructed of a non-elastic material.

Figure 12:
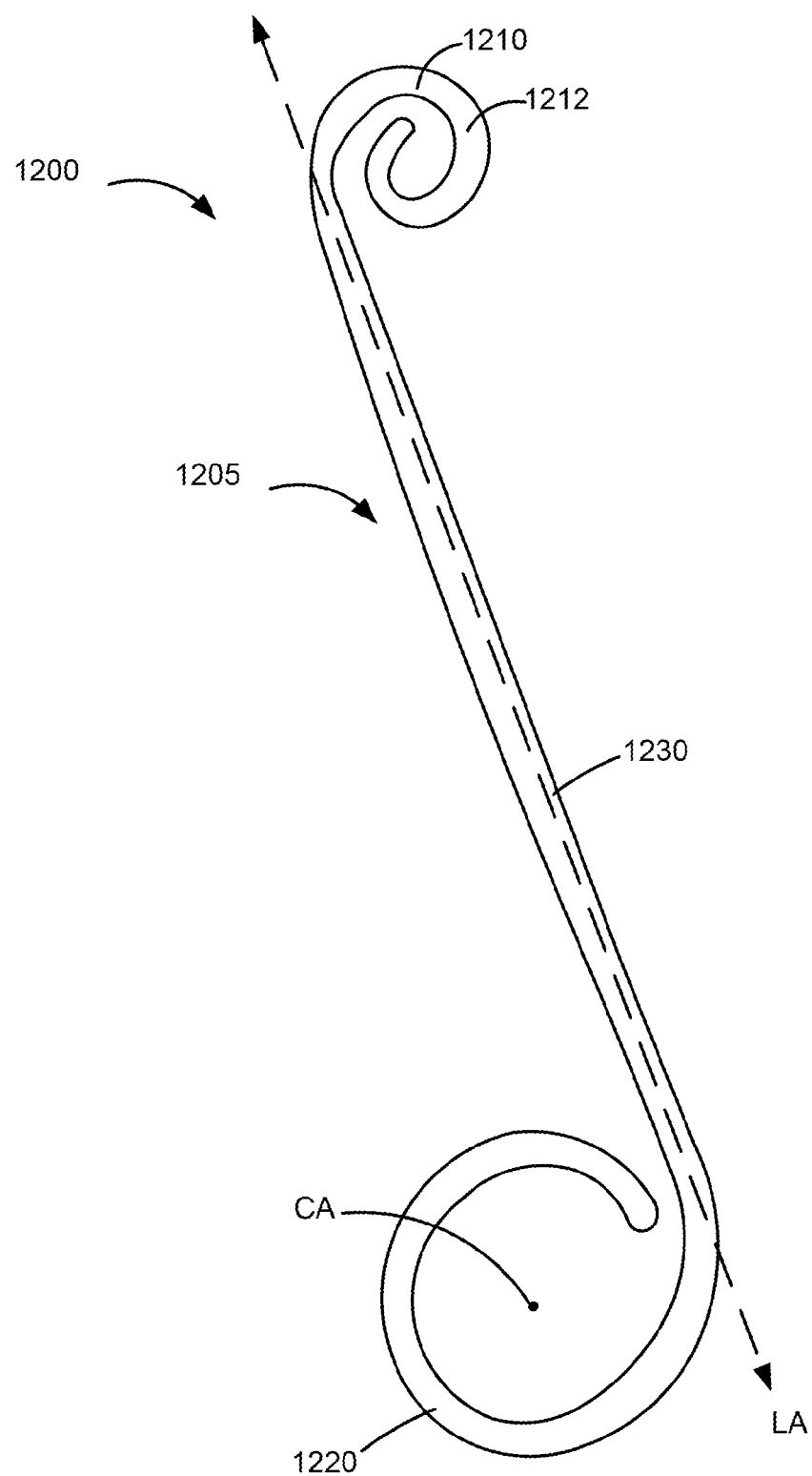

FIG. 12 is a perspective view of a medical device 1200. The medical device 1200 includes an elongate member 1205 that has a distal end portion 1210, a proximal end portion 1220, and a medial portion 1230. In one embodiment, the medical device 1200 is a ureteral stent and is configured to help facilitate the flow of fluid from one portion of the body to another portion of the body.

The distal end portion 1210 is configured to be placed in a kidney of the patient and includes a retention member 1212. The retention member 1212 is configured to help retain the medical device 1200 in place within the body of the patient.

The medial portion 1210 is configured to be placed in the ureter of the patient and defines a longitudinal axis LA.

The proximal end portion 1220 is configured to be placed in a bladder of the patient and is configured to distend or otherwise retain the bladder in an expanded configuration. The proximal end portion 1220 includes a coil portion 1222. The coil portion 1220 is configured to contact the bladder to help retain the bladder in an expanded configuration. In some embodiments, the coil portion 1222 is configured to contact the bladder at various locations (for example, at various locations of the inner wall of the bladder) to help retain the bladder in an expanded configuration. In some embodiments, the coil portion 1222 is configured to avoid contact with the trigone region of the patient.

Figure 13:
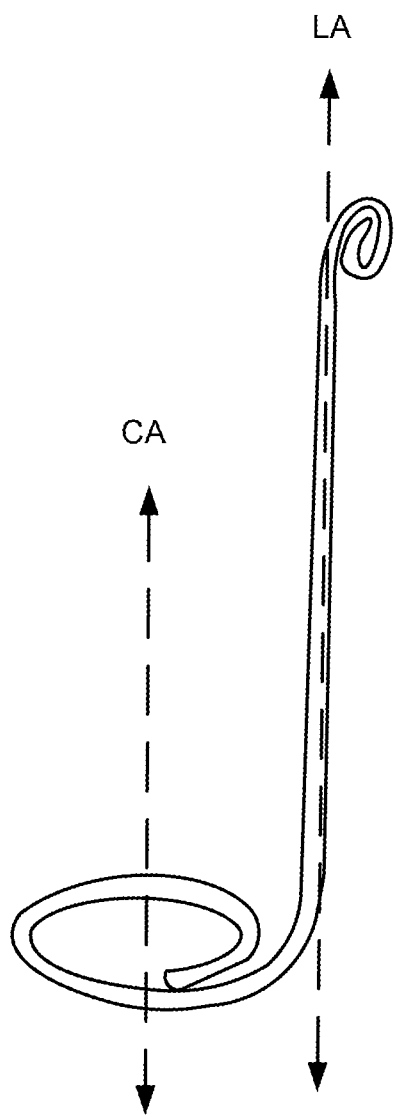

The coil portion 1222 coils about a coil axis CA that is different than the longitudinal axis LA defined by the medial portion 1130. In the illustrated embodiment, the coil axis CA is substantially perpendicular to the longitudinal axis LA. In other embodiments, the coil axis CA is not perpendicular to the longitudinal axis LA. For example, as illustrated in FIG. 13, in one embodiment the coil axis CA is substantially parallel to the longitudinal axis LA.

Figure 14:
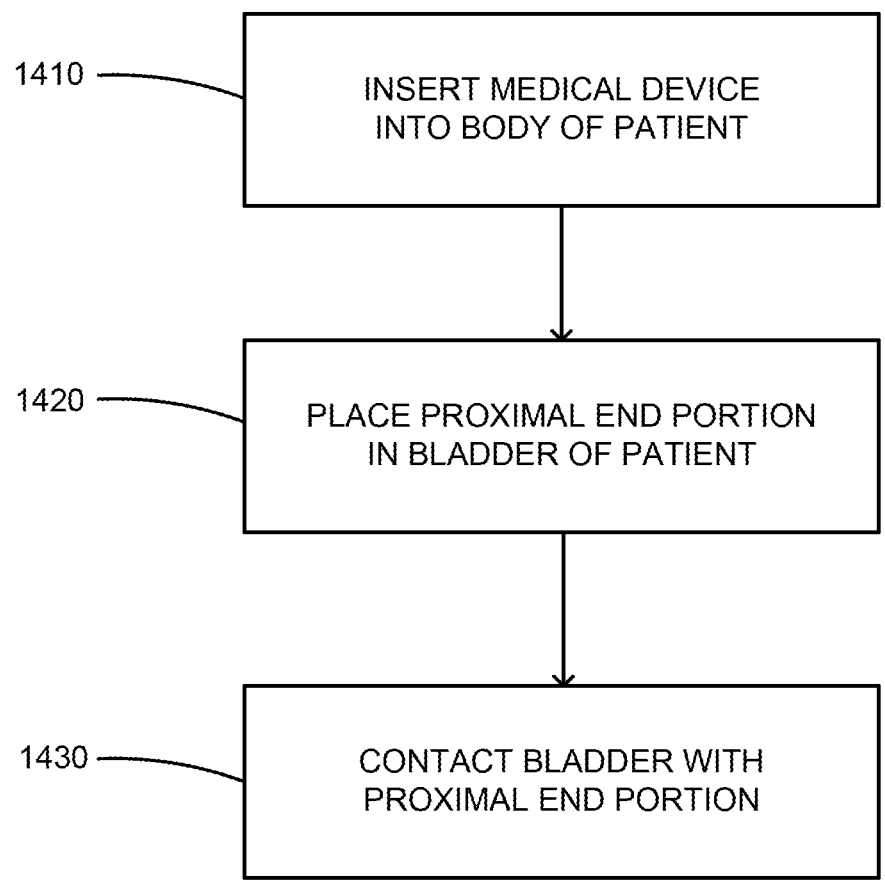
FIG. 14 is a flow chart of a method of placing a medical device according to an embodiment of the invention.

FIG. 14 is a flow chart illustrating a method of placing a medical device into a body of a patient. At step 1410, the medical device is inserted into the body of the patent. At step 1420, the medical device is oriented such that a proximal end portion of the medical device is disposed within a bladder of the patient. At step 1430, the proximal end portion is caused to contact the bladder to distend or otherwise retain the bladder in an expanded configuration.

In some embodiments, the method of placing the medical device also includes inflating an inflatable portion of the medical device. In some embodiments, the method also includes forming or adjusting the shape of the proximal end portion of the medical device.

In some embodiments a medical device, comprises an elongate member having a distal end portion, a proximal end portion, and a medial portion disposed between the distal end portion an the proximal end portion. The proximal end portion is configured to be disposed within a bladder of a patient and a portion of the proximal end portion is configured to contact the bladder to help retain the bladder in an expanded configuration.

In some embodiments, the proximal end portion of the elongate member is configured to avoid the trigone region of the patient. In some embodiments, the proximal end portion of the elongate member includes a malecot having a plurality of arms. In some embodiments, the proximal end portion includes a first arm and a second arm. The first arm is configured to contact an inner wall of the bladder of the patient at a first location. The second arm is configured to contact the inner wall of the bladder of the patient at a second location. The second location is different than the first location.

In some embodiments, the distal end portion includes a retention member that is configured to be disposed within a kidney of the patient and to help retain at least a portion of the medical device within the kidney of the patient. In some embodiments, the proximal end portion includes a coil. In some embodiments, the proximal end portion includes a coil. A first portion of the coil is configured to contact an inner wall of the bladder of the patient at a first location. A second portion of the coil is configured to contact the inner wall of the bladder of the patient at a second location. The second location is different than the first location.

In some embodiments, the proximal end portion includes a coil. The coil is coiled about a coil axis. The coil axis is substantially parallel to an axis defined by the medial portion of the elongate member. In some embodiments, the proximal end portion includes a coil. The coil is coiled about a coil axis. The coil axis is substantially perpendicular to the axis defined by the medial portion of the elongate member. In some embodiments, the proximal end portion includes an inflatable portion.

In some embodiments, the proximal end portion includes a first portion including a first material and a second portion including a second material. The first material is softer than the second material.

In some embodiments, a medical device comprises an elongate member having a distal end portion, a proximal end portion, and a medial portion disposed between the distal end portion and the proximal end portion. The distal end portion includes a first material, the medial portion includes a second material, and the proximal end portion includes a third material. The second material is softer than the first material, and the second material is softer than the third material.

In some embodiments, the first material and the third material are the same material. In some embodiments, the proximal end portion includes a first arm portion and a second arm portion. The first arm portion is configured to contact a bladder of a patient at a first location. The second arm portion is configured to contact the bladder of the patient at a second location different than the first location.

In some embodiments, the proximal end portion includes an arm that has a first portion and a second portion. The first portion of the arm is disposed between the distal end portion of the elongate member and the second portion of the arm. The first portion of the arm includes the second material. The second portion of the arm includes the third material. In some embodiments, the proximal end portion is configured to contact an inner portion of a bladder of a patient and to help retain the bladder in an expanded condition. In some embodiments, the proximal end portion includes a malecot. In some embodiments, the proximal end portion is configured to be disposed in a bladder of a patient and to avoid contact with a trigone region of the patient.

In some embodiments, a method of placing a medical device within a patient comprises inserting a medical device having a distal end portion, a proximal end portion, and a medial portion disposed between the distal end portion and the proximal end portion into a body of a patient, and causing the proximal end portion to contact a bladder of the patient to help retain the bladder in an expanded configuration.

In some embodiments, the inserting includes placing the distal end portion of the medical device into the bladder of the patient.

While certain features of the described implementations have been illustrated as described herein, many modifications, substitutions, changes and equivalents will now occur to those skilled in the art. It is, therefore, to be understood that the appended claims are intended to cover all such modifications and changes as fall within the scope of the embodiments.

What is claimed is:

1. A medical device, comprising:
an elongate member having a distal end portion, and a proximal end portion, the distal end portion including a first retention member configured to be disposed within a kidney of a patient, the proximal end portion including a second retention member configured to be disposed within a bladder of the patient, the elongate member including a medial portion disposed between the distal end portion and the proximal end portion, the medial portion being of a length configured to extend from the kidney to the bladder,
the first retention member including a first material that extends an entire length of the first retention member, the medial portion including a second material such that the second material extends along the length of the medial portion and into a distal end portion of the second retention member, the second retention member including a proximal end portion having a third material,
wherein prior to implantation within the patient each of the first material, the second material, and the third material includes a different respective biocompatible plastic having different respective first, second and third durometer values, the second material having a lower durometer value than the first material, the second material having a lower durometer value than the third material, the first material having a durometer of between 86 and 90 shore A, the second material having a durometer of between 82 and 86 shore A, and the third material having a durometer of between 86 and 95 shore A, the medical device being co-extruded.

2. The medical device of claim 1, wherein the second retention member of the elongate member is configured to avoid a trigone region of the patient.

3. The medical device of claim 1, wherein the second retention member of the elongate member includes a malecot having a plurality of arms, wherein only a portion of each of the plurality of arms that is proximal to the medial portion is composed of the second material and other portions of each of the plurality of arms are composed of the third material.

4. The medical device of claim 1, wherein the second retention member includes a first arm and a second arm, the first arm being configured to contact an inner wall of the bladder of the patient at a first location, the second arm being configured to contact the inner wall of the bladder of the patient at a second location, the second location being different than the first location, wherein only a portion of each of the first arm and the second arm that is proximal to the medial portion is composed of the second material and other portions of the first arm and the second arm are composed of the third material.

5. A medical device comprising:
an elongate member having a distal end portion, and a proximal end portion, the distal end portion including a first retention member configured to be disposed within a kidney of a patient, the proximal end portion including a second retention member configured to be disposed within a bladder of the patient, the elongate member including a medial portion disposed between the distal end portion and the proximal end portion, the medial portion being of a length configured to extend from the kidney to the bladder,
the first retention member being composed of a first material, the medial portion being composed of a second material such that the second material extends along the length of the medial portion and into a distal end portion of the second retention member, the second retention member including a proximal end portion being composed of a third material,
wherein prior to implantation within the patient each of the first material, the second material, and the third material includes a different respective biocompatible plastic having different respective first, second and third durometer values, the second material having a lower durometer value than the first material, the second material having a lower durometer value than the third material, the first material having a durometer of between 86 and 90 shore A, the second material having a durometer of between 82 and 86 shore A, and the third material having a durometer of between 86 and 95 shore A, the medical device being co-extruded.

6. The medical device of claim 5, wherein the second retention member includes a first arm and a second arm, the first arm being configured to contact the bladder of the patient at a first location, the second arm being configured to contact the bladder of the patient at a second location different than the first location, wherein only a portion of each of the first arm and the second arm that is proximal to the medial portion is composed of the second material and other portions of the first arm and the second arm are composed of the third material.

7. The medical device of claim 5, wherein the second retention structure is configured to contact an inner portion of the bladder of the patient to retain the bladder in an expanded configuration.

8. The medical device of claim 5, wherein the second retention structure includes a malecot having a plurality of arms, wherein only a portion of each of the plurality of arms that is proximal to the medial portion is composed of the second material and other portions of each of the plurality of arms are composed of the third material.

9. The medical device of claim 5, wherein the second retention structure is configured to be disposed in the bladder of the patient and to avoid contact with a trigone region of the patient.

10. A device comprising:
an elongate member having a distal end portion, and a proximal end portion, the distal end portion including a retention member configured to be disposed within a kidney of a patient, the proximal end portion including a malecot configured to be disposed within a bladder of the patient, the elongate member including a medial portion disposed between the distal end portion and the proximal end portion, the medial portion being of a length configured to extend from the kidney to the bladder, the retention member of the distal end portion of the elongate member being entirely composed of a first material, the malecot including a distal end portion composed of the second material and a proximal end portion composed of a third material, wherein prior to implantation within the patient each of the first material, the second material, and the third material includes a different respective biocompatible plastic having different respective first, second and third durometer values, the second material having a lower durometer value than the first material, the second material having a lower durometer value than the third material, the first material having a durometer of between 86 and 90 shore A, the second material having a durometer of between 82 and 86 shore A, and the third material having a durometer of between 86 and 95 shore A, the device being co-extruded.

11. The device of claim 10, wherein the malecot includes a first arm and a second arm, the first arm being configured to contact the bladder of the patient at a first location, the second arm being configured to contact the bladder of the patient at a second location different than the first location.

12. The device of claim 10, wherein the malecot is configured to contact an inner portion of the bladder of the patient to retain the bladder in an expanded configuration.

13. The medical device of claim 10, wherein the malecot is configured to be disposed in the bladder of the patient and to avoid contact with a trigone region of the patient.

* * * * *